Figure 1:
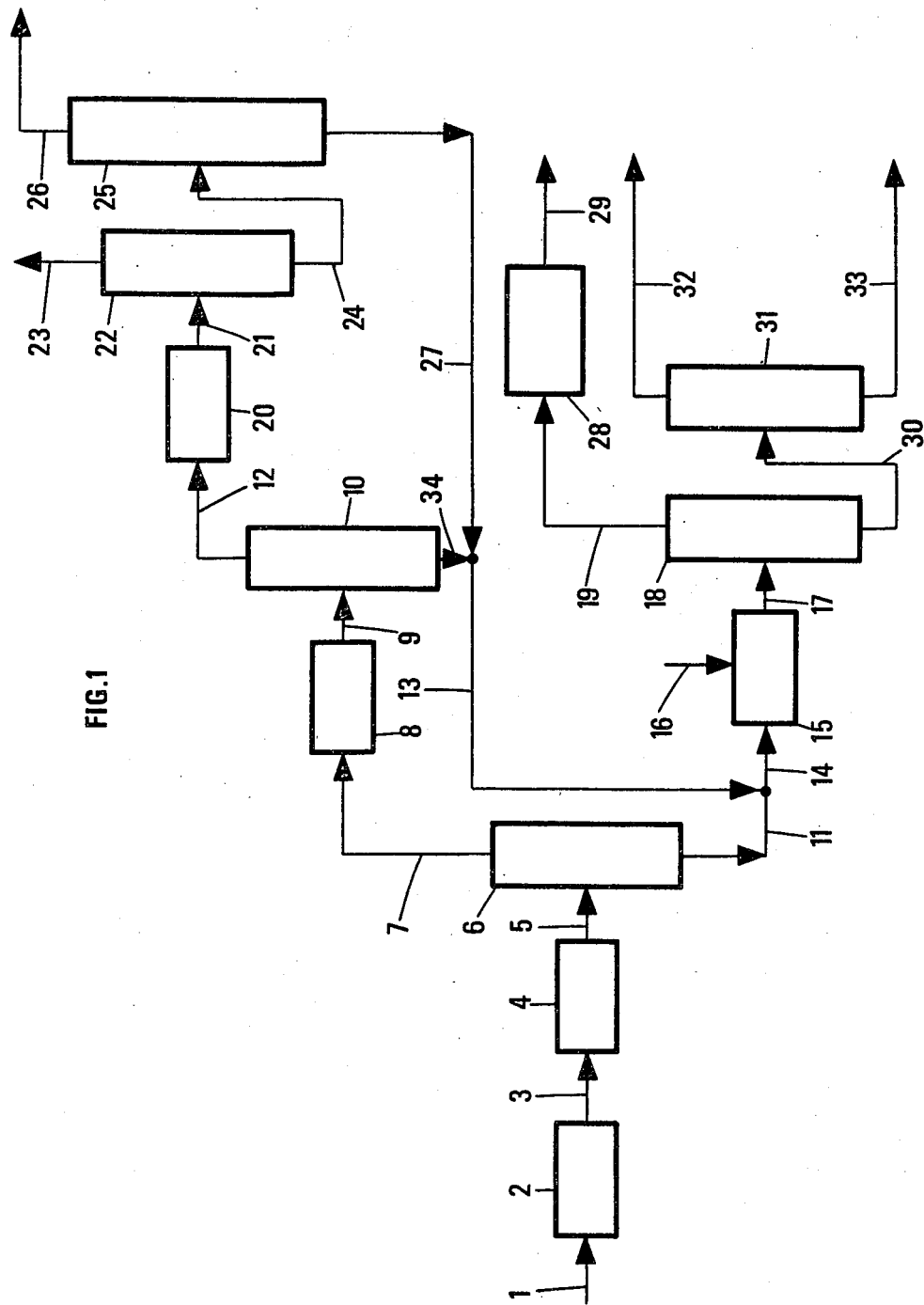

ized *United States Patent* [19]

Juguin et al.

[11] 4,423,264
[45] Dec. 27, 1983

[54] PROCESS FOR THE JOINT PRODUCTION OF HIGHLY PURE 1-BUTENE AND PREMIUM GASOLINE FROM A $C_4$ OLEFINIC CUT

[75] Inventors: Bernard Juguin, Rueil-Malmaison; Jean Cosyns, Maule; Jean Miquel, Paris, all of France

[73] Assignee: Institut Francais du Petrole, Rueil-Malmaison, France

[21] Appl. No.: 392,056

[22] Filed: Jun. 25, 1982

[30] Foreign Application Priority Data

Jun. 26, 1981 [FR] France ............................. 81 12795
Jul. 2, 1981 [FR] France ............................. 81 13211
Dec. 8, 1981 [FR] France ............................. 81 23065

[51] Int. Cl.$^3$ ............................................. C07C 2/74
[52] U.S. Cl. ................................... 585/255; 585/254; 585/329
[58] Field of Search .................... 585/254, 255, 329

[56] References Cited

U.S. PATENT DOCUMENTS

| | | | |
|---|---|---|---|
| 4,244,806 | 1/1981 | Le Page et al. | 585/255 |
| 4,268,700 | 5/1981 | Vu | 585/329 |
| 4,324,646 | 4/1982 | Le Page et al. | 585/255 |
| 4,324,938 | 4/1982 | Cosyns et al. | 585/329 |
| 4,367,356 | 1/1983 | Ward | 585/329 |

*Primary Examiner*—Curtis R. Davis
*Attorney, Agent, or Firm*—Millen & White

[57] ABSTRACT

Highly pure 1-butene and premium gasoline are obtained by (a) subjecting a $C_4$ olefinic cut to a polymerization-disproportionation to partly convert the isobutene thereof to a gasoline which, in turn, by partial disproportionation, yields a jet fuel base and butenes, (b) fractionating the effluent from step (a) to a mixture ($\alpha$) of gasoline and jet fuel base and to a fraction ($\beta$) containing isobutane, n-butane, butenes, a small amount of isobutene and a minor amount of butadiene, (c) selectively polymerizing fraction ($\beta$) to convert more than 90% of the isobutene thereof to gasoline, (d) fractionating the polymerized fraction ($\beta$) to a gasoline cut ($\gamma$) containing isobutene dimers and trimers and to a fraction ($\delta$) containing isobutane, n-butane and butenes, (e) selectively hydrogenating the fraction ($\delta$), (f) removing isobutane from the hydrogenated fraction ($\delta$) and (g) fractionating the deisobutanized hydrogenated fraction ($\delta$) to obtain a fraction containing at least 99% of 1-butene, the mixture ($\alpha$) being admixed with the cut ($\gamma$).

22 Claims, 3 Drawing Figures

PROCESS FOR THE JOINT PRODUCTION OF HIGHLY PURE 1-BUTENE AND PREMIUM GASOLINE FROM A C4 OLEFINIC CUT

The present invention concerns a process for the joint production of 1-butene of a purity higher than 99%, of premium gasoline, and optionally, of ethylene, propene and jet fuel, said process being made possible by a judicious combination of several steps. The initial charge is generally a C4 olefinic cut issued, for example, from a steam-cracking zone.

The process according to the invention is adapted to petrochemical plants including a steam-cracking unit and permits a better upgrading of the butene cuts which, in most cases, are in excess.

The process according to the invention enables one to obtain in particular:

(1) 1-butene of high purity with very high yields; the 1-butene content at the output of the process is clearly higher than that of the 1-butene initially contained in the feed charge, (2) premium gasoline, (3) jet fuel of high quality and, optionally, ethylene and propene.

The process of the invention is characterized in that:

(a) an olefinic C4 cut, which generally, at this stage, contains isobutane, n-butane, 1-butene, 2-butenes, isobutene and optionally butadiene (generally less than 2% and preferably less than 0.7% by weight of butadiene) is subjected to a polymerization disproportionation in which, on the one hand, the isobutene of said cut is converted at least partly to gasoline and, on the other hand, the so-produced gasoline is subjected at least partly to a partial disproportionation reaction so as to recover, on the one hand, a jet fuel base type cut and, on the other hand, 2-butenes and mainly 1-butene produced by said disproportionation, (b) the effluent withdrawn from the polymerization-disproportionation zone is subjected to a fractionation giving, on the one hand, a mixture ($\alpha$) of gasoline and jet fuel base and, on the other hand, a fraction ($\beta$) consisting essentially of isobutane, n-butane, 1-butene, 2-butenes and a minor proportion of isobutene (generally lower than 5% and preferably lower than 2% by weight), (c) the cut ($\beta$) obtained in step (b) is fed to a selective polymerization zone called finishing polymerization zone, wherein more than 90% of the residual isobutene is converted to gasoline, (d) the effluent withdrawn from said finishing polymerization zone of step (c) is subjected to a fractionation giving, on the one hand, a cut ($\gamma$) formed in major part of gasoline containing mainly a mixture of dimers and trimers of isobutene and 1- and 2-butenes and, on the other hand, a fraction ($\delta$) consisting essentially of isobutane, n-butane, 1-butene, 2-butenes, a minor proportion of isobutene (generally lower than 0.3% and preferably lower than 0.15% by weight), and butadiene traces (generally less than 100 parts per million), (e) the cut ($\delta$) issued from step (d) is fed to a selective hydrogenation zone so as to reduce its butadiene content to a maximum of 10 parts per million by weight with respect to the 1-butene of said cut, (f) the effluent from the selective hydrogenation step (e) is fed to a deisobutanization zone in view of removing the major part of the isobutane contained therein, (g) the so-deisobutanized fraction is subjected to a fractionation giving, on the one hand, a cut containing a major part of 2-butenes and n-butane, and, on the other hand, a fraction formed of at least 99% by weight of 1-butene, the mixture ($\alpha$) formed by the gasoline and the jet fuel base issued from step (b) being admixed with the gasoline cut ($\gamma$) produced in step (d).

Figure 2:
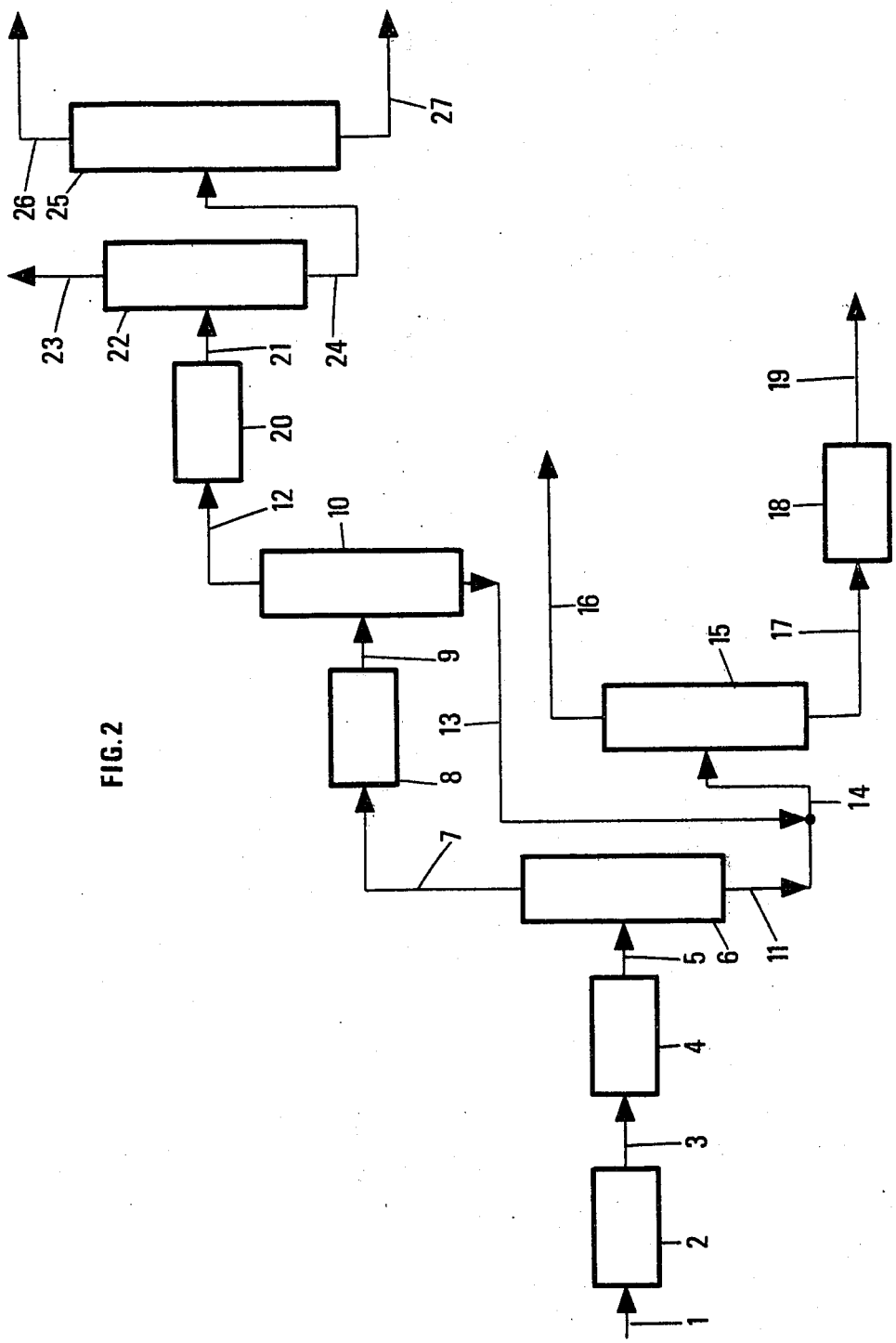
Figure 3:
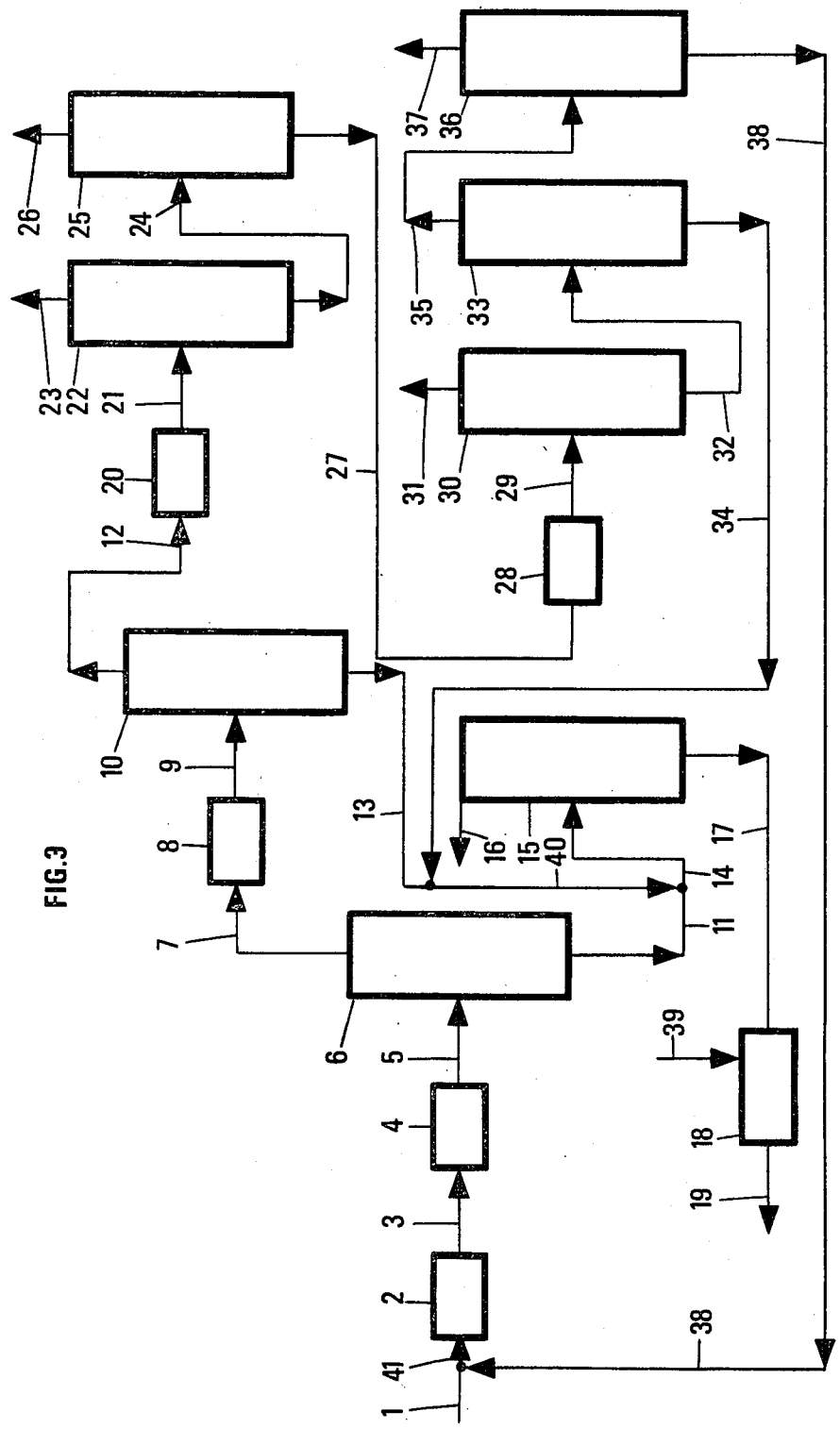

The three FIGS. 1 to 3 illustrate three particular embodiments of the invention.

The process illustrated in FIG. 1 is characterized in that:

(a) A C4 olefinic cut which generally, at this stage, contains isobutane, n-butane, 1-butene, 2-butenes, isobutene and, optionally, butadiene (generally less than 2% and preferably less than 0.7% by weight of butadiene), may be first fed to a drying zone (drying achieved in a conventional manner, for example by passing the cut over a molecular sieve, preferably a sieve of the 3A type), then subjected to a polymerization-disproportionation in which, on the one hand, the isobutene of said cut is converted at least partly to gasoline and, on the other hand, the so-produced gasoline is subjected at least partly to a partial disproportionation reaction so as to recover, on the one hand, a cut of the jet fuel base type, and, on the other hand, 2-butenes and mainly 1-butene produced by said disproportionation, (b) the effluent withdrawn from the polymerization-disproportionation zone is subjected to a fractionation giving, on the one hand, a mixture ($\alpha$) of gasoline and jet fuel base and, on the other hand, a fraction ($\beta$) consisting essentially of isobutane, n-butane, 1-butene, 2-butenes, a minor proportion of isobutene (generally lower than 5% and preferably lower than 2% by weight), and a minor amount of butadiene (generally lower than 2000 parts per million and preferably lower than 500 parts per million), (c) the cut ($\beta$) obtained in step (b) is fed to a selective polymerization zone called finishing polymerization zone, wherein more than 90% of the residual isobutene is converted to gasoline, whereas only a small proportion of 1-butene and 2-butenes is converted to gasoline, (d) the effluent withdrawn from the so-called finishing polymerization zone of step (c) is subjected to a fractionation giving, on the one hand, a cut ($\gamma$) formed in major part of gasoline containing mainly a mixture of dimers and trimers of isobutene and 1-and 2-butenes, and, on the other hand, a fraction ($\delta$) consisting essentially of isobutane, n-butane, 1-butene, 2-butenes, a minor proportion of isobutene (generally lower than 0.3% and preferably lower than 0.15% by weight), and butadiene traces (generally lower than 100 parts per million), (e) the cut ($\delta$) produced in step (d) is fed to a selective hydrogenation zone so that its butadiene content be reduced to a maximum of 10 parts per million by weight with respect to the 1-butene of said cut, (f) the effluent from the selective hydrogenation step (e) is fed to a deisobutanization zone in order to remove the major part of the isobutane contained therein, (g) the so-deisobutanized fraction is subjected to a fractionation giving, on the one hand, a cut containing a major portion of 2-butenes and n-butane and, on the other hand, a fraction containing a minimum of 99% by weight of 1-butene, said 1-butene fraction being, in particular, perfectly adapted to be used, directly as comonomer in the production of high density polyethylene, (h) the mixture (α) of gasoline and jet fuel base produced in step (b) is admixed with the gasoline cut (γ) produced in step (d) and with the C₄ cut containing a high proportion of 2-butenes and n-butane produced in step (g), the new resulting mixture being then subjected to a generally complete hydrogenation, (i) the hydrogenation effluent from step (h) being subjected to one or more fractionations in view to obtain a n-butane cut (which is generally fed to a steam-cracking zone, e.g. that from which is supplied the C₄ cut treated according to the invention, where it will be converted mainly to ethylene and propene: as a matter of fact, n-butane forms with n-hexane the charge which, after ethane, gives the best yields of ethylene), a gasoline cut of high octane number which may be supplied to a gasoline pool and a jet fuel cut of excellent quality.

In the polymerization-disproportionation reaction of step (a), isobutene is essentially converted to a gasoline formed essentially of isobutene dimers and trimers.

The cut of the jet fuel base type contains a major proportion of isobutene trimers and tetramers.

In the so-called finishing polymerization zone, the isobutene and a small part of the 1- and 2-butenes are converted to isobutene dimers and trimers.

In the so-called polymerization-disproportionation zone, the conditions are such that isobutene reacts up to a conversion rate to gasoline higher than 95% by weight, whereas 1- and 2-butenes are not only unconverted but their concentration is increased by the reaction of disproportionation of a part of the gasoline formed from the isobutene.

In the so-called finishing polymerization zone, the conditions are such that the isobutene reacts up to conversion rates higher than 90% by weight, whereas the total conversions of the normal butenes (1-butene and 2-cis- and trans-butenes) remain lower or equal to 10% by weight and, preferably, lower than 7%.

The polymerization-disproportionation reactions are effected in liquid phase, in the presence of a catalyst, for example, in fixed bed, at a temperature of about 10° to 120° C., under a pressure from 0.3 to 10 MPa (preferably the temperature is from about 30° to 80° C. and the pressure from 0.5 to 3 MPa), with a liquid hydrocarbon flow rate (Space Velocity) of about 0.05 to 2 volumes per volume of catalyst and per hour.

The so-called finishing polymerization reaction is also effected in liquid phase in the presence of a catalyst, for example, in fixed bed, at a temperature of about 30° to 200° C., under a pressure from about 0.5 to 20 MPa (preferably the temperature is about 50° to 150° C. and the pressure from 1 to 10 MPa), with a liquid hydrocarbon flow rate (Space velocity) of about 0.2 to 4 volumes per volume of catalyst and per hour.

The catalysts of the acid type are selected from the silica-aluminas, the silica-magnesiae, the boron-aluminas, phosphoric acid deposited on kieselguhr, silica or quartz and from catalysts of the "solid phosphoric acid" type, i.e. a catalyst formed of a siliceous substance of great absorbing power, impregnated with a high proportion of phosphoric acid, mixtures of optionally co-precipitated alumina gel and thoria, with optional additions of chromium oxide, zinc oxide or an equivalent metal oxide. Other catalysts can be selected from those obtained by treating a transition alumina with an acid fluorine compound, with the optional addition of a silicic ester. Preferably, there is used a silica-alumina whose silica content is from 60 to 95% by weight and, preferably, from 70 to 90%, containing, as additive, from 0.1 to 5% by weight of chromium oxide and/or zinc oxide. The presence of chromium oxide is preferred for the polymerization-disproportionation, that of zinc oxide for the finishing polymerization.

The butadiene selective hydrogenation reaction is effected in the presence of a catalyst, for example as fixed bed, said catalyst consisting of metals or of associations of hydrogenating metals deposited on a substantially neutral carrier, for example, a Pd/Al₂O₃ or Pd+Ag/Al₂O₃ catalyst. The reaction temperature will be from 10° to 100° C., the pressure from 0.1 to 3 MPa (preferably the temperature is from about 20° to 60° C. and the pressure from 0.5 to 1.5 MPa), with a liquid hydrocarbon flow rate (space velocity) of from about 2 to 20 volumes per volume of catalyst and per hour, the hydrogen/butadiene molar ratio, at the reactor input, being from 0.5 to 5.

The hydrogenation reaction of the mixture of 2-butenes, gasoline and jet fuel type base, is effected in the presence of a catalyst, for example as fixed bed, said catalyst consisting of a hydrogenating metal deposited on a substantially neutral carrier, for example the catalyst sold under reference LD 265 by PROCATALYSE Corporation. The reaction temperature is from 150° to 400° C., the pressure from 2 to 10 MPa (preferably the temperature is from about 220° to 300° C. and the pressure from 4 to 6 MPa), the liquid hydrocarbon flow rate (space velocity) from about 1 to 5 volumes per volume of catalyst and per hour, the hydrogen/hydrocarbons molar ratio at the reactor input being from 2 to 10.

FIG. 1 illustrates the invention.

The olefinic C₄ charge is introduced through line 1 into the optional drying zone 2 wherefrom it is withdrawn through line 3 to be fed to the polymerization disproportionation zone 4. The effluent from the polymerization-disproportionation zone is conveyed through line 5 to the fractionation zone 6. In line 11, there is recovered essentially a mixture of isobutene dimers, trimers and tetramers, i.e., a mixture of premium gasoline and jet fuel base. Through line 7, a fraction is withdrawn which contains generally, at this stage, isobutane, n-butane, 1-butene, 2-butenes, a small amount of isobutene and a minor amount of butadiene and which is fed to the finishing polymerization zone 8. The effluent from the finishing polymerization zone is conveyed through line 9 to the fractionation zone 10. There is recovered, from line 13, a mixture of dimers and trimers of isobutene, 1-butene and 2-butenes, i.e. a premium gasoline which is admixed in line 14 with the premium gasoline jet fuel base cut issued from line 11;

From line 12, there is generally withdrawn, at this stage, isobutane, n-butane, 1-butene, 2-butenes, a very small amount of isobutene and butadiene traces, which are fed to the selective hydrogenation zone 20. The effluent from the selective hydrogenation zone is supplied, through line 21, to the deisobutanization zone 22 from the top of which are withdrawn, through line 23, isobutane and 1-butene, as well as a small amount of 2-butenes and isobutene; from the bottom of the column, through line 24, there is recovered a mixture containing essentially 1-butene and 2-butenes. The mixture from line 24 is fractionated in the superfractionation zone 25. There is thus obtained, on the one hand, through line 26, 1-butene with traces of isobutane and isobutene (said fraction contains at least 99% by weight of 1-butene), and on the other hand, through line 27, a mixture containing mainly n-butane, 2-butenes and a small amount of 1-butene, said mixture being then admixed, in a first stage, with gasoline issued through line 34 from the so-called finishing polymerization zone and, in a second stage, with the polymerizate issued from the polymerization-disproportionation zone through line 11.

The resultant mixture is then introduced through line 14 into the hydrogenation zone 15 where, in the presence of hydrogen introduced through line 16, said mixture is subjected to a complete hydrogenation. The product obtained from said hydrogenation zone is supplied through line 17, for example, to a first fractionation column 18.

At the top of said column is withdrawn essentially n-butane which can be fed, through line 19, to a steam-cracking unit 28 (for example that from which is issued the $C_4$ cut treated according to the invention) where this n-butane is converted to a large extent to ethylene, propene and gasoline (line 29).

From the bottom of column 18, there is recovered a mixture of gasoline and jet fuel which is fed through line 30 to a second fractionation column 31. At the top of said column, is withdrawn a gasoline which can be supplied to a gasoline pool through line 32 and, from the bottom of the column, through line 33, a jet fuel of high quality.

EXAMPLE 1 illustrating FIG. 1

In this example, the treated charge issuing from a steam cracking and wherefrom the major part of butadiene has been removed, has the following composition in percents by weight:

| | |
|---|---|
| isobutene | 1.3 |
| n-butane | 6.4 |
| 1-butene | 27.9 |
| 2-butenes | 14.5 |
| isobutene | 49.6 |
| butadiene | 0.3 |
| | 100 |

It is first subjected to drying with a molecular sieve 3A (zone 2 of the figure), then it is fed, through line 3, to a polymerization-disproportionation unit 4 containing a catalyst which is a silica-alumina having a 85% by weight silica content and to which has been further added 0.2% by weight of chromium, as chromium nitrate.

The operating conditions are as follows:
Pressure: 2 MPa
Temperature: 50° C.
Space velocity VVH: 0.3

The obtained effluent is subjected to a fractionation (zone 6 of the figure).

From the bottom of the column, through line 11, is recovered a polymerizate amounting to 26.45% by weight of the initial charge.

From the top of the column, through line 7, is withdrawn a fraction having the following composition in % by weight with respect to the initial charge.

| | |
|---|---|
| Isobutane | 2.64 |
| n-butane | 8.77 |
| 1-butene | 39.92 |
| 2-butenes | 20.76 |
| isobutene | 1.43 |
| butadiene | 0.03 |
| | 73.55 |

This fraction from line 7 is fed to a finishing polymerization unit 8 containing a catalyst which consists of a silica-alumina having a 85% by weight silica content, to which has been further added, 0.2% by weight of zinc, as zinc nitrate.

The operating conditions are as follows:
Pressure: 2 MPa
Temperature: 80° C.
Space velocity VVH: 0.5

The obtained effluent is then subjected to a fractionation (zone 10 of the figure).

From the bottom of the column, through line 13, is recovered a gasoline amounting to 3.75% by weight with respect to the initial charge. This gasoline is then admixed with the polymerizate issued from line 11.

From the top of the column 10, through line 12, is withdrawn a fraction having the following composition by weight with respect to the initial charge:

| | |
|---|---|
| isobutane | 3.30 |
| n-butane | 9.18 |
| 1-butene | 36.28 |
| 2-butenes | 20.94 |
| isobutene | 0.10 |
| butadiene | 40 ppm |
| | ~69.80 |

This fraction from line 12 is fed to a butadiene selective hydrogenation unit 20 containing a hydrogenation catalyst, sold by PROCATALYSE Corporation under reference LD 271.

The operating conditions are as follows:
Pressure: 1 MPa
Temperature: 40° C.
Space velocity VVH: 10
Hydrogen/butadiene: 2 moles/1 mole The obtained effluent is then fed through line 21 to a deisobutanization unit 22, formed of two serially arranged columns of 65 plates each. Through line 23, is recovered a cut containing, by weight with respect to the initial charge:

| | |
|---|---|
| isobutane | 3.14 |
| n-butane | 0 |
| 1-butene | 1.78 |
| 2-butenes | 0.46 |
| isobutene | 0.07 |
| | 5.45 |

Through line 24, is recovered a cut having the following composition, by weight with respect to the initial charge:

| | |
|---|---|
| isobutane | 0.16 |
| n-butane | 9.18 |
| 1-butene | 34.50 |
| 2-butenes | 20.48 |
| isobutene | 0.03 |
| butadiene | 0 |
| | 64.35 |

This cut is fractionated in a superfractionation zone 25. The fraction withdrawn at the top of the column through line 26 contains, by weight with respect to the initial charge:

| | |
|---|---|
| isobutane | 0.16 |

|  |  |
|---|---|
| isobutene | 0.03 |
| 1-butene | 32.84 |
|  | 33.03 |

The 1-butene of said cut thus has a purity of 99.4%.

From the bottom of the superfractionation column 25 is recovered a fraction containing, by weight with respect to the initial charge:

|  |  |
|---|---|
| n-butane | 9.18 |
| 1-butene | 1.66 |
| 2-butenes | 20.48 |
|  | 31.32 |

This fraction is then admixed in lines 27 and 13, in a first stage, with gasoline issuing, through line 34, from the finishing polymerization zone and then, in a second stage, with the polymerizate from line 11 issued from the polymerization-disproportionation zone 4.

The resultant mixture is then conveyed through line 14 to the hydrogenation zone 15 where the product is subjected, in the presence of a catalyst (sold by PROCATALYSE Corporation under reference LD 265) and hydrogen supplied from line 16, to a complete hydrogenation under the following operating conditions:

Pressure: 5 MPa
Input temperature of the reactor: 30° C.
Output temperature of the reactor: 290° C.
Space velocity VVH: 2
Hydrogen/hydrocarbon molar ratio: 5/1

The effluent from the complete hydrogenation zone is fed through line 17 to a first fractionation column 18. From the top of said first column is withdrawn, through line 19, n-butane amounting to 32.11% by weight of the initial charge.

This n-butane is recycled to the steam-cracking zone 28. The effluent from said steam-cracking zone, withdrawn through line 29, has the following composition, by weight with respect to the initial charge:

|  |  |
|---|---|
| hydrogen | 0.74 |
| methane | 6.94 |
| acetylene | 0.06 |
| ethylene | 13.23 |
| ethane | 0.29 |
| propene | 5.27 |
| propadiene | 0.74 |
| n-butenes | 0.29 |
| pentadiene | 0.19 |
| isopentene | 0.03 |
| steam-cracking gasoline | 4.33 |
|  | 32.11 |

From the bottom of the first fractionation column 18, is recovered a product which is fed through line 30 to a second fractionation column 31.

From the top of said second column is withdrawn, through line 32, a gasoline amounting to 24.73% by weight of the initial charge and whose main characteristics are as follows:

|  |  |
|---|---|
| Specific gravity at 15° C. | 0.745 |
| Octane numbers |  |
| RON clear | 97 |
| RON ethylated at 0.5°/₀₀ | 104 |
| MON clear | 90 |
| MON ethylated at 0.5°/₀₀ | 98 |
| ASTM distillation |  |
| IP | 96° C. |
| 5% vol | 101° C. |
| 10% | 105° C. |
| 20% | 112° C. |
| 30% | 120° C. |
| 40% | 127° C. |
| 50% | 141° C. |
| 60% | 160° C. |
| 70% | 171° C. |
| 80% | 177° C. |
| 90% | 186° C. |
| 95% | 193° C. |
| Final point | 204° C. |
| Distillate | 99.5% vol |
| residue | 0.5% vol |
| losses | — |

This gasoline may be directly fed to a gasoline pool, since it complies with all the characteristics and specifications concerning premium gasolines.

From the bottom of said second fractionation column 31 is recovered, through line 33, a jet fuel amounting to 5.88% by weight of the initial charge and whose main characteristics are as follows:

Crystallization point: <−65° C.
Smoke point: 33 mm

The process corresponding to FIG. 2 is characterized in that:

(a) an olefinic $C_4$ cut, which generally at this stage contains isobutane, n-butane, 1-butene, 2-butenes, isobutene and optionally butadiene (generally less than 2% and preferably less than 0.7% by weight of butadiene), is optionally first fed to a drying zone (drying effected in a conventional manner, for example by passage of the cut over a molecular sieve, preferably a sieve of 3A type), then is subjected to a polymerization-disproportionation in which, on the one hand, the isobutene of said cut is converted at least partly to gasoline and, on the other hand, the so-produced gasoline is subjected at least partly to a partial disproportionation reaction so as to recover, on the one hand, a jet fuel base type cut and, on the other hand, 2-butenes and mainly 1-butene produced by said disproportionation, (b) the effluent withdrawn from the polymerization-disproportionation zone is subjected to a fractionation giving on the one hand, a mixture ($\alpha$) of gasoline and jet fuel base and, on the other hand, a fraction ($\beta$) consisting essentially of isobutane, n-butane, 1-butene, 2-butenes, a small proportion of isobutene (generally lower than 5% and preferably lower than 2% by weight) and a minor amount of butadiene (generally smaller than 2000 parts per million and preferably less than 500 parts per million), (c) the fraction ($\beta$) obtained in step (b) is fed to the selective polymerization zone called finishing polymerization zone, wherein more than 90% of the residual isobutene is converted to gasoline, while only a very small proportion of 1-butene and 2-butenes is converted to gasoline, (d) the effluent withdrawn from the so-called finishing polymerization zone of step (c) is subjected to a fractionation giving, on the one hand, a cut ($\gamma$) formed in major part of gasoline containing in particular a mixture of dimers and trimers of isobutene and 1- and 2-butenes and, on the other hand, a fraction ($\delta$) consisting essentially of isobutane, n-butane, 1-butene, 2-butenes, a minor proportion of isobutene (generally less than 0.3% and preferably less than 0.15% by weight) and butadiene traces (generally lower than 100 parts per million), (e) the cut (δ) issued from step (d) is fed to a selective hydrogenation zone so as to reduce its butadiene content to a maximum of 10 parts per million by weight with respect to the 1-butene of said cut, (f) the effluent from the selective hydrogenation step (e) is fed to a deisobutanization zone in order to remove the major part of the isobutane contained therein, (g) the so-deisobutanized fraction is subjected to a fractionation giving, on the one hand, a cut containing a major part of the 2-butenes and of the n-butane and, on the other hand, a fraction containing at least 99% by weight of 1-butene; said 1-butene cut being perfectly convenient, in particular, for direct use as co-monomer in the production of high density polyethylene, (h) the mixture (α), consisting of gasoline and jet fuel base, issued from step (b), is admixed with the gasoline cut (γ) issued from sted (d), the new resulting mixture being subjected to a fractionation giving, on the one hand, a gasoline cut of high octane number (premium gasoline) which may be fed to a gasoline pool and, on the other hand, a cut which can be used as jet fuel base (mixture of isobutene trimers and tetramers).

The jet fuel base cut issued from step (h) is optionally fed to a hydrogenation zone at the output of which is obtained a product having excellent qualities as jet fuel.

During the polymerization-disproportionation reaction of step (a) the isobutene is essentially converted to a gasoline formed essentially of isobutene dimers and trimers. The jet fuel base type cut contains a major proportion of isobutene trimers and tetramers.

In the so-called finishing polymerization zone, the isobutene and a small part of 1- and 2-butenes are converted to isobutene dimers and trimers.

In the so-called polymerization-disproportionation zone the conditions are such that the isobutene reacts up to conversion rates to gasoline higher than 95% by weight, whereas 1- and 2-butenes are not only unconverted, but their concentration is increased by the disproportionation reaction of a portion of the gasoline formed from isobutene.

In the so-called finishing polymerization zone the conditions are such that the isobutene reacts up to conversion rates higher than 90% by weight, whereas the total conversions of normal butenes (1-butene and 2-cis and trans-butenes) remain lower than or equal to 10% by weight and preferably lower than 7%.

The polymerization-disproportionation reactions are effected as shown in FIG. 1.

The so-called finishing polymerization reaction is also effected as illustrated in FIG. 1.

The hydrogenation reaction of the jet fuel type cut is effected as shown in FIG. 1.

FIG. 2 illustrates the invention:

The C$_4$ olefinic charge is introduced through line 1 into an optional drying zone 2, wherefrom it is withdrawn through line 3 and fed to the polymerization-disproportionation zone 4. The effluent from the polymerization-disproportionation zone is conveyed through line 5 to the fractionation zone 6. Through line 11 is recovered essentially a mixture of isobutene dimers, trimers and tetramers, i.e. a mixture of premium gasoline and jet fuel base. Through line 7 is withdrawn a fraction containing, generally, at this stage, isobutane, n-butane, 1-butene, 2-butenes, a small amount of isobutene and a minor amount of butadiene and which is fed to the finishing polymerization zone 8.

The effluent from the finishing polymerization zone is conveyed through line 9 to the fractionation zone 10. From line 13 is recovered a mixture of dimers and trimers of isobutene, 1-butene and 2-butenes, i.e. a premium gasoline which is admixed in line 14 with the premium gasoline-jet fuel base cut issued from line 11: the resulting mixture is introduced through line 14 into the fractionation zone 15. From line 16 is essentially withdrawn a premium gasoline which can be supplied to the gasoline pool. Through line 17 is recovered a mixture of isobutene trimers and tetramers, i.e. a jet fuel base which can be fed to the hydrogenation zone 18. The effluent of the hydrogenation zone 19 forms a jet fuel of high quality.

Through line 12 is generally withdrawn, at this stage, isobutane, n-butane, 1-butene, 2-butenes, a small amount of isobutene and butadiene traces which are fed to the selective hydrogenation zone 20. The effluent of the selective hydrogenation zone is fed through line 21 to the deisobutanization zone 22 wherefrom is withdrawn at the top, through line 23, isobutane and 1-butene as well as small amounts of 2-butenes and isobutene; from the bottom of the column, through line 24, is recovered a mixture containing essentially 1-butene and 2-butenes. The mixture from line 24 is fractionated in the superfractionation zone 25. There is thus obtained, on the one hand, from line 27, 2-butenes, n-butane and a small amount of 1-butene and, on the other hand, through line 26, 1-butene with traces of isobutane and isobutene. The fraction conveyed through duct 26 contains at least 99% by weight of 1-butene. It thus constitutes a 1-butene fraction of a purity higher than 99%.

EXAMPLE 2 illustrating FIG. 2

The treated charge, issuing from a steam cracking and from which the major portion of butadiene has been removed, has the following composition by weight:

| | |
|---|---|
| isobutene | 1.3 |
| n-butane | 6.4 |
| 1-butene | 27.9 |
| 2-butenes | 14.5 |
| isobutene | 49.6 |
| butadiene | 0.3 |
| | 100 |

It is first subjected to drying with a molecular sieve 3 A (zone 2 of the Figure), then it is fed through line 3 to a polymerization-disproportionation unit 4 containing a catalyst consisting of a silica-alumina with a 85% by weight silica content, to which chromium nitrate has further been added so as to introduce 0.3% by weight of Cr$_2$O$_3$.

The operating conditions are as follows:
Pressure: 2 MPa
Temperature: 50° C.
Space velocity VVH: 0.3

The obtained effluent is subjected to a fractionation (zone 6 of the Figure).

At the bottom of the column there is recovered, through line 11, a polymerizate amounting to 26.45% by weight of the initial charge.

From the top of the column, through line 7, is withdrawn a fraction having the following composition in percent by weight with respect to the initial charge:

| | |
|---|---|
| isobutane | 2.64 |
| n-butane | 8.77 |
| 1-butene | 39.92 |
| 2-butenes | 20.76 |
| isobutene | 1.43 |
| butadiene | 0.03 |
| | 75.33 |

This fraction from line 7 is fed to a finishing polymerization unit 8 containing a catalyst consisting of silica-alumina with a 85% by weight silica content, to which has been further added 0.25% by weight of ZnO in the form of zinc nitrate.

The operating conditions are as follows:
Pressure: 2 MPa
Temperature: 50° C.
Space velocity VVH: 0.5

The obtained effluent is then subjected to a fractionation (zone 10 of the Figure).

From the bottom of the column, through line 13, is recovered a gasoline amounting to 3.75% by weight with respect to the initial charge. This gasoline is then admixed with the polymerizate issued from line 11; the resulting mixture is conveyed through line 14 to the fractionation zone 15.

From the top of the column, through line 16, is withdrawn a gasoline amounting to 24.38% of the initial charge and which has the following characteristics:

| | |
|---|---|
| Specific gravity at 15° C. | 0.757 |
| Octane numbers | |
| RON clear | 100 |
| RON ethylated at 0.5°/oo | 103.5 |
| MON clear | 85 |
| MON ethylated at 0.5°/oo | 88 |
| ASTM distillation | |
| IP | 100° C. |
| 5% | 105° C. |
| 10% | 109° C. |
| 20% | 116° C. |
| 30% | 123° C. |
| 40% | 130° C. |
| 50% | 144° C. |
| 60% | 163° C. |
| 70% | 174° C. |
| 80% | 181° C. |
| 90% | 188° C. |
| 95% | 195° C. |
| FP | 206° C. |
| distillate | 99.5% |
| residue | 0.5% |
| losses | — |

This gasoline may be directly fed to the gasoline pool without being subjected to an other fractionation or purification step.

From the bottom of the column, through line 17, is recovered a heavier polymerizate which may be used as jet fuel base; this heavy polymerizate is fed to a hydrogenation zone 18 containing a hydrogenation catalyst consisting of an alumina having a surface of 70 m$^2$/g and a 0.3% by weight palladium content.

The operating conditions are as follows:
Pressure: 5 MPa
Temperature: 290° C.
Space velocity VVH: 2
Molar ratio hydrogen/hydrocarbons: 5/1

The effluent 19 from the hydrogenation zone amounts to 5.88% by weight of the initial charge. It forms a jet fuel of high quality; its main characteristics are as follows:
Crystallization point: $<-65°$ C.
Smoke point: 33 mm From the top of column 10, through line 12, is withdrawn a fraction having the following composition by weight with respect to the initial charge:

| | |
|---|---|
| isobutane | 3.30 |
| n-butane | 9.18 |
| 1-butene | 36.28 |
| 2-butenes | 20.94 |
| isobutene | 0.10 |
| butadiene | 40 ppm |
| | 69.80 |

This fraction from line 12 is fed to a butadiene selective hydrogenation unit 20 containing a hydrogenation catalyst comprising 0.2% by weight of palladium and 0.2% by weight of silver on alumina having a surface of 15 m$^2$/g.

The operating conditions are as follows:
Pressure: 1 MPa
Temperature: 40° C.
Space velocity VVH: 10
Hydrogen/butadiene ratio: 2 moles/1 mole The obtained effluent is then fed through line 21 to a deisobutanizing unit 22, formed of two serially connected columns of 65 plates each. Through line 23 is recovered a cut containing, by weight with respect to the initial charge:

| | |
|---|---|
| isobutane | 3.14 |
| n-butane | 0 |
| 1-butene | 1.78 |
| 2-butenes | 0.46 |
| isobutene | 0.07 |
| | 5.45 |

Through line 24 is recovered a cut of the following composition by weight with respect to the initial charge:
isobutane: 0.16
n-butane: 9.18
1-butene: 34.50
2-butenes: 20.48
isobutene: 0.03
butadiene: 0

This cut is fractionated in a superfractionation zone 25. From the bottom of column 27 is recovered a fraction containing, by weight with respect to the initial charge:

| | |
|---|---|
| n-butane | 9.18 |
| 1-butene | 1.66 |
| 2-butenes | 20.48 |
| | 31.32 |

The fraction withdrawn from the top of the column through line 26 contains, by weight with respect to the initial charge:

| | |
|---|---|
| isobutane | 0.16 |
| isobutene | 0.03 |
| 1-butene | 32.84 |

| |
|---|
| 33.03 |

The purity of 1-butene from said cut is thus 99.4%.

As hereinbefore disclosed, butadiene is hydrogenated in the presence of a catalyst containing palladium and silver on a carrier. This catalyst has the advantage, as compared with a catalyst containing only palladium on a carrier, to avoid the undesirable isomerization of 1-butene. This catalyst may contain from 0.05 to 0.5% by weight of palladium and from 0.05 to 1% by weight of silver, the silver/palladium ratio by weight ranging from 0.7:1 to 3:1, preferably from 1:1 to 2.5:1. The carrier is preferably alumina (preferred specific surface: 1–100 m$^2$/g) or silica (preferred specific surface: 10–200 m$^2$/g).

The process according to FIG. 3 is an improvement to that illustrated in FIG. 2. It is conceived in such a manner that:

(a) the fresh charge, consisting essentially of an olefinic C$_4$ cut which, generally at this stage, contains isobutane, n-butane, 1-butene, 2-butenes, isobutene and optionally butadiene (generally less than 2% and preferably less than 0.7% by weight of butadiene) is optionally fed first to a drying zone, where the drying is effected in a conventional manner, for example by passage of the cut over a molecular sieve (preferably a sieve of the 3 A type). Thereafter, the fresh charge is subjected to polymerization-disproportionation in which, on the one hand, a portion of the isobutene of said cut is converted at least partly to gasoline (isobutene dimers and trimers) and, on the other hand, the so-produced gasoline is subjected at least partly to a partial disproportionation reaction so as to recover a cut of the jet fuel base type (mixture of isobutene trimers and tetramers), 2-butenes and mainly 1-butene, (b) the effluent withdrawn from the polymerization-disproportionation zone of step (a) is subjected to a fractionation giving, on the one hand, a mixture (α) of gasoline and jet fuel base and, on the other hand, a fraction (β) consisting essentially of isobutane, n-butane, 1-butene, 2-butenes, a small proportion of isobutene (generally lower than 5% and, preferably, lower than 2% by weight) and a minor amount of butadiene (generally less than 2 000 parts per million and, preferably less than 500 parts per million), (c) the fraction (β) obtained in step (b) is fed to a selective polymerization zone called finishing polymerization zone, wherein more than 90% of the residual isobutene is converted to gasoline, while only a small portion of 1-butene and 2-butenes of the fraction (β) are converted to gasoline, (d) the effluent withdrawn from the so-called finishing polymerization zone of step (c) is subjected to a fractionation giving on the one hand, a cut (γ) formed in major part of gasoline (or premium gasoline) containing in particular a mixture of dimers and trimers of isobutene and 1- and 2-butenes and, on the other hand, a fraction (δ) consisting essentially of isobutene, n-butane, 1-butene, 2-butenes, a minor proportion of isobutene (generally less than 0.3% and preferably less than 0.15% by weight), and butadiene traces (generally less than 100 parts per million by weight), (e) the cut (δ) issued from step (d) is then fed to a so-called selective hydrogenation zone so as to reduce its butadiene content to a maximum of 10 parts per million by weight with respect to the 1-butene of said cut, (f) the effluent from the selective hydrogenation step (e) is fed to a deisobutanization zone in order to remove at least the major part of the isobutane contained therein, (g) the so-deisobutanized fraction is subjected to a fractionation giving on the one hand, a cut (ε) containing in major part 2-butenes and n-butane and, on the other hand, a fraction containing at least 99% by weight of 1-butene, said 1-butene fraction being perfectly convenient in particular for direct use as co-monomer in the production of high density polyethylene, the process according to the invention being further characterized in that:

(h) said cut (ε) containing in major part the 2-butenes and n-butane, issued from step (g), is fed to an isomerization zone wherein at least a portion of these 2-butenes is isomerized to isobutene and 1-butene, without affecting the major portion of n-butane (a small portion of the cut (ε) is converted by cracking to ethane, ethylene and propene, another small portion is converted to isobutane and n-butane by hydrogen transfer reaction and another small portion of the 2-butenes from cut (ε) is converted to gasoline), (i) the product issued from the isomerization zone of step (h) is first fed to a first fractionation column, at the top of which is withdrawn a cut containing mainly ethane, ethylene and propene and from the bottom of which is recovered a fraction containing mainly 1-butene, 2-butenes, isobutene, isobutane traces, n-butane and a small gasoline proportion, this latter fraction being then fed to a second fractionation column, from the bottom of which is recovered the small gasoline fraction and at the top of which is withdrawn a mixture containing 1-butene, isobutene, 2-butenes and and n-butane (together with a very small amount of isobutane), (j) the mixture obtained in the preceding step is fed to an extractive distillation column at the top of which is removed the major portion of isobutane and n-butane (which otherwise would tend to accumulate in the circuit), the fraction recovered at the bottom of the solvent extraction distillation column (and which at this stage mainly contains 1-butene, isobutene, 2-butenes and a small amount of n-butane) is recycled to the input of an optional dryer or at least to the input of the polymerization-disproportionation zone, where it is thus admixed with the fresh charge, and, (k) said mixture (α) of gasoline and jet fuel base, issued from step (b), is combined, on the one hand, with the gasoline obtained at the bottom of the second fractionation column of step (i) and, on the other hand, with the cut (α) obtained in step (d), the resulting mixture being fed to a fractionation zone, at the top of which is recovered a premium gasoline which may be fed to the gasoline pool, and from the bottom of which is recovered a product which is optionally subjected, at least partly, to a total hydrogenation, at the end of which is recovered a jet fuel of high quality.

The comments about the various involved reactions are the same as those indicated for the two first flow sheets.

As concerns more particularly the so-called isomerization reaction of step (h), it can be effected in gaseous phase, preferably in the presence of steam, with a catalyst arranged in fixed or moving or expanded bed, or in a fluid bed, at a temperature of about 400° to 600° C., under a pressure from about 0.01 to 2 MPa (preferably the temperature is from about 460° to 530° C. and the pressure from 0.1 to 0.5 MPa), with a flow rate of liquid hydrocarbons (space velocity) of about 0.5 to 4 volumes per volume of catalyst and per hour, the molar ratio steam/hydrocarbons being between 0.2 and 2. In said isomerization zone, preferably at least 40% (or better 45%) of the 2-butenes are converted to isobutene and 1-butene whereas at least 80% and preferably 90% of the n-butane remain unconverted.

For this isomerization reaction of step (h), the selected catalysts are fluorinated catalysts obtained for example by treatment of a transition alumina with a fluorine compound, for example hydrofluoric acid, ammonium fluoride, fluorosilicic acid, fluoroboric acid, fluoroorganic compounds, as described in the French patent No. 2.484.400.

The optional hydrogenation reaction of the jet fuel type base (step k) is effected in the presence of a catalyst arranged, for example, as a fixed bed, said catalyst being formed of a hydrogenating metal deposited on a substantially neutral carrier, for example the catalyst sold by PROCATALYSE Corporation, under reference LD 265. The reaction temperature is generally from 150° to 400° C., the pressure from 2 to 10 MPa (preferably the temperature is from about 220° to 300° C. and the pressure from 4 to 6 MPa), the liquid hydrocarbon flow rate (Space velocity) being from about 1 to 5 volumes per volume of catalyst and per hour and the molar ratio hydrogen/hydrocarbons at the reactor input being from 2 to 10.

The extractive distillation, by solvent, of isobutane and n-butane is effected in the presence of solvents selected for example from the group consisting of acetonitrile, dimethylformamide, N-methylpyrrolidone. The temperature is generally from −10° C. to 220° C. (preferably from 50° to 180° C.) and the pressure from 0.1 to 1 MPa (preferably from 0.3 to 0.7 MPa). The solvent ratio is more particularly selected from 1 to 10 by weight (preferably from 2 to 6 by weight).

FIG. 3 illustrates the invention:

The $C_4$ olefinic charge is introduced through line 1 into the optional drying zone 2, wherefrom it is supplied, through line 3, to the polymerization-disproportionation zone 4. The effluent from the polymerization-disproportionation zone is conveyed through line 5 to the fractionation zone 6. Through line 11, there is recovered essentially a mixture of isobutene dimers, trimers and tetramers, i.e. a mixture of premium gasoline and jet fuel base. Through line 7 is withdrawn a fraction generally containing, at this stage, isobutane, n-butane, 1-butene, 2-butenes, a small amount of isobutene and a minor amount of butadiene, which is fed to the finishing polymerization zone 8. The effluent from the finishing polymerization zone is conveyed through line 9 to the fractionation zone 10. Through line 13, there is recovered a mixture of dimers and trimers of isobutene, 1-butene and 2-butenes, i.e. a premium gasoline which is fed through line 40 to be admixed, in line 14, with the premium gasoline-jet fuel base cut issued from line 11. Through line 12 is generally withdrawn, at this stage, isobutane, n-butane, 1-butene, 2-butenes, a small amount of isobutene and butadiene traces, which are fed to the selective hydrogenation zone 20. The effluent from the selective hydrogenation zone is supplied, through line 21, to the deisobutanization zone 22, wherefrom is withdrawn, at the top, through line 23, isobutane and 1-butene as well as a small amount of 2-butenes and isobutene; from the bottom of the column, through line 24, is recovered a mixture containing essentially 1-butene and 2-butenes. The mixture from line 24 is fractionated in the superfractionation zone 25. There is thus obtained, on the one hand, from line 26, 1-butene with traces of isobutane and isobutene (the 1-butene content of said fraction is at least 99% by weight), and, on the other hand, from line 27, a mixture containing mainly n-butane, 2-butenes and a small amount of 1-butene; this latter mixture is then supplied to an isomerization zone 28. The product issued from the isomerization zone is fed through line 29 to a first fractionation column 30; at the top of said column is withdrawn, through line 31, a fraction containing essentially ethane, ethylene and mainly propene, and which can be used as fuel or as petrochemical charge; from the bottom of column 30 is recovered a product containing mainly isobutane, n-butane, 1-butene, isobutene, 2-butenes and gasoline, said product being fed through line 32 to a second fractionation colum 33. From the bottom of said column is recovered a gasoline supplied through line 34 to line 13 for being admixed in line 40 with gasoline issuing, through line 13, from the fractionation zone 10, the resulting mixture being in turn admixed with the polymerizate from line 11 issued from the fractionation zone 6. From the top of column 33 is withdrawn a product containing mainly isobutane, n-butane, 1-butene, isobutene and 2-butenes; this product is fed through line 35 to an extractive distillation zone 36. From the top of said extractive distillation zone is withdrawn, through line 37, a product containing mainly isobutane an particularly, n-butane. From the bottom of the extractive distillation zone is recovered a fraction containing essentially 1-butene, isobutene and 2-butenes, said fraction being then recycled, through lines 38 and 41, to the inlet of the drying zone 2 (or of zone 4) where it is admixed with the fresh charge (it must be observed that from the bottom of the extractive distillation column, the butenes and isobutene are generally recovered in the extraction solvent. The solvent is removed by mere distillation or by stripping or by re-extraction by means of a non-miscible auxiliary solvent, such as a paraffinic hydrocarbon easily separable by distillation of the butenes and isobutene).

The gasolines from lines 13 and 34, in admixture in line 40, and the polymerizate of line 11, are supplied together, through line 14, to a fractionation zone 15. From the top of said column is withdrawn, essentially, through line 16, a premium gasoline which can be fed to the gasoline pool. From the bottom of the column is recovered, through line 17, a mixture of isobutene trimers and tetramers, i.e. a jet fuel base, which can be supplied to a total or partial hydrogenation zone 18, the required hydrogen being introduced through line 39; at the output from said hydrogenation zone is recovered, through line 19, a jet fuel of high quality.

EXAMPLE 3: illustrating FIG. 3:

The balance-sheet of materials in the various sections of the total unit is shown in Table I.

The treated charge amounts to 100 kg and has the following composition by weight:

| | |
|---|---|
| isobutane | 1.3 |
| n-butane | 6.4 |
| 1-butene | 27.9 |
| isobutene | 49.6 |
| 2-butenes | 14.5 |

-continued

| | |
|---|---|
| 1,3-butadiene | 0.3 |
| | 100 |

At the end of the process, the following products are obtained:
1-butene (purity 99.6): 42.5 kg
Premium gasoline: 31.1 kg
Jet fuel: 7.2 kg The purity of 1-butene is 99.5%; accordingly it may be used as co-monomer in the production of high density polyethylene:

The octane number of the premium gasoline is:
RON clear = 100

The jet fuel is of very good quality:
Crystallization point: < −65° C.
Smoke point: 35 mm The operating conditions in this example are as follows:

The charge is dried (zone 2) with a molecular sieve 3 A.

The polymerization-disproportionation zone 4 operates at 50° C. under 2 MPa, with a VVH of 0.3, in the presence of a catalyst consisting of a silica-alumina with a 85% by weight silica content, to which has been further added chromium nitrate so as to introduce 0.3% by weight of $Cr_2O_3$ into the catalyst. The finishing polymerization zone 8 operates at 50° C., under 2 MPa, with a VVH of 0.5, in the presence of a catalyst consisting of a silica-alumina having a 85% by weight silica content, to which has been further added 0.25% by weight of zinc oxide in the form of zinc nitrate. The hydrogenation zone 18 operates at 290° C., under 5 MPa, with a VVH of 2 and a molar ratio hydrogen/hydrocarbons of 5/1, in the presence of a hydrogenation catalyst containing 0.3% by weight of palladium on an alumina having a surface of 70 m$^2$/g. The selective hydrogenation zone 20 operates at 40° C., under 1 MPa, with a VVH of 10 and a ratio hydrogen/butadiene of 2 moles/1 mole, in the presence of a catalyst consisting of an alumina having a surface of 15 m$^2$/g, containing 0.2% by weight of palladium and 0.2% by weight of silver. The deisobutanizing unit 22 is formed of two serially connected columns having each 65 plates. The isomerization in zone 28 is effected in the presence of steam at 450° C. under 0.1 MPa with a VVH of 2 and a molar ratio $H_2O$/HC of 1.30, in the presence of a catalyst used as alumina balls (of the γ cubic type) of 1 to 2 mm diameter, having the following characteristics:
Specific gravity: 1.23
Structural density: 3.27
Total pore volume: 0.57 cc/g
Specific surface: 200 m$^2$/g
and having the following composition:
Content of alkali metals lower than 100 ppm (by weight)
Content of alkaline earth metals lower than 300 ppm (by weight)
Content by weight of fluorine: 1%

The extractive distillation column 36 contains 60 plates. The solvent, which is dimethylformamide, is fed to the column at the 8th plate from the top, at a flow rate equal to 4.2 times the feeding rate. The top vapors are condensed and one half of the condensate is recycled to the top of the column, as reflux, whereas the other half of the condensate is discharged from the system.

EXAMPLE 3A (comparative)

The preceding example is repeated, but in the absence of the isomerization section 28, of its related devices (fractionation columns 30 and 33) and of the extractive distillation column 36 and consequently without effecting the recycling through lines 13, 34 and 38.

From 100 kg of charge having the composition given in the preceding example, the following net productions are obtained:
1-butene (purity 99.4%): 32.84 kg
Premium gasoline: 24.38 kg
Jet fuel: 5.88 kg These results show the advantage to operate according to the process of the invention.

What is claimed is:

1. A process for producing highly pure 1-butene and premium gasoline from $C_4$ olefinic cut, characterized in that:
(a) a $C_4$ olefinic cut which, at this stage, contains isobutane, n-butane, 1-butene, 2-butenes, isobutene and butadiene, is subjected to a polymerization-disproportionation during which, on the one hand, the isobutene of said cut is converted at least partly to gasoline and, on the other hand, the so-produced gasoline is subjected at least partly to a reaction of partial disproportionation so as to recover, on the one hand, a cut of the jet fuel base type and, on the other hand,

TABLE I

BALANCE-SHEET OF MATERIALS IN THE VARIOUS SECTIONS OF THE UNIT

| REFERENCE NUMBERS OF THE LINES IN THE FIG. | 1 | 3 | 7 | 11 | 12 | 13 | 23 | 26 | 27 | 31 | 34 | 37 | 38 | 16 | 39 | 19 |
|---|---|---|---|---|---|---|---|---|---|---|---|---|---|---|---|---|
| Hydrogen | | | | | | | | | | | | | | | 0.05 | |
| ethane | | | | | | | | 0.02 | | | | | | | | |
| ethylene | | | | | | | | 0.10 | | | | | | | | |
| propene | | | | | | | | 0.77 | | | | | | | | |
| isobutane | 0.90 | 0.90 | 2.03 | | 2.68 | | 2.55 | 0.13 | — | | | 0.06 | | | | |
| n-butane | 4.42 | 5.04 | 7.07 | | 7.47 | | — | — | 7.47 | | | 7.06 | 0.62 | | | |
| 1-butene | 19.28 | 26.05 | 33.84 | | 32.30 | | 1.58 | 29.25 | 1.47 | 0.09 | | 0.06 | 6.77 | | | |
| isobutene | 34.27 | 41.92 | 1.22 | | 0.10 | | 0.07 | 0.03 | — | 28 ppm | | 0.07 | 7.65 | | | |
| 2-butenes | 10.03 | 25.87 | 33.43 | | 31.40 | | 0.69 | | 30.71 | | | 0.15 | 15.84 | | | |
| 1-3 butadiene | 0.21 | 0.22 | 0.02 | | 30 ppm | | — | — | — | | | | 0.01 | | | |
| polymerizate | | | | 22.39 | | | | | | | | | | | | |
| gasoline | | | | | | 3.66 | | | | | 0.38 | | | 21.50 | | |
| jet fuel | | | | | | | | | | | | | | | | 4.98 |
| TOTAL | 69.11 | 100 | 77.61 | 22.39 | 73.95 | 3.66 | 4.89 | 29.41 | 39.65 | 0.98 | 0.38 | 7.40 | 30.89 | 21.50 | 0.05 | 4.98 |

2-butenes and mainly 1-butene produced by said disproportionation, (b) the effluent withdrawn from the polymerization-disproportionation zone is subjected to a fractionation giving, on the one hand, a mixture ($\alpha$) of gasoline and jet fuel base and, on the other hand, a fraction ($\beta$) consisting essentially of isobutane, n-butane, 1-butene, 2-butenes, a minor proportion of isobutene and a minor amount of butadiene, (c) the cut ($\beta$) obtained in step (b) is fed to a selective polymerization zone called finishing polymerization zone, wherein more than 90% of the residual isobutene is converted to gasoline, (d) the effluent withdrawn from said finishing polymerization zone of step (c) is subjected to a fractionation giving, on the one hand, a cut ($\gamma$) consisting in major part of gasoline containing a mixture of dimers and trimers of isobutene and of 1- and 2-butenes and, on the other hand, a fraction ($\delta$) consisting essentially of isobutane, n-butane, 1-butene, 2-butenes, a minor proportion of isobutene, (less than 0.3% and butadiene traces, less than 100 parts per million), (e) the cut ($\delta$) issued from step (d) is fed to a selective hydrogenation zone so as to reduce its butadiene content to a maximum of 10 parts per million by weight with respect to the 1-butene of said cut, (f) the effluent from the selective hydrogenation step (e) is supplied to a deisobutanization zone is order to remove the major part of the isobutane contained therein, (g) the so-deisobutanized fraction is subjected to a fractionation giving on the one hand, a cut containing a major portion of 2-butenes and n-butane and, on the other hand, a fraction containing at least 99% by weight of 1-butene, and the mixture ($\alpha$) formed by the gasoline and the jet fuel base obtained in step (b) is admixed with the gasoline cut ($\gamma$) obtained in step (d).

2. A process according to claim 1 for producing highly pure 1-butene and premium gasoline from a $C_4$ olefinic cut characterized in that:

(a) a $C_4$ olefinic cut containing isobutane, n-butane, 1-butene, 2-butenes, isobutene and less than 2% by weight of butadiene is subjected in a zone (4) to a polymerization-disproportionation, effected in liquid phase, during which on the one hand, the isobutene of said cut is essentially converted at least partly to gasoline and, on the other hand, at least a portion of said gasoline is converted to 1-butene and 2-butenes and to a jet fuel base type cut, (b) the effluent withdrawn from the polymerization-disproportionation zone (4) is subjected to a fractionation in zone (6) giving, on the one hand, a mixture ($\alpha$) of gasoline and jet fuel base and, on the other hand, a fraction ($\beta$) essentially consisting of isobutane, n-butane, 1-butene, 2-butenes, less than 5% by weight of isobutene and less than 2000 ppm of butadiene, (c) the fraction ($\beta$) obtained in step (b) is fed to a selective, called finishing polymerization zone 8 wherein 90% at least, by weight, of the isobutene contained therein are converted to gasoline, the selective polymerization reaction being effected in liquid phase, (d) the effluent from the finishing polymerization zone is subjected to a fractionation (zone 10) during which is recovered, on the one hand, a cut ($\gamma$) consisting in major part of gasoline containing dimers and trimers of isobutene and of 1- and 2-butenes and, on the other hand, a fraction ($\delta$) essentially consisting of isobutane, n-butane, 1-butene, 2-butenes, less than 0.3% by weight of isobutene and less than 100 ppm of butadiene, (e) the cut ($\delta$) obtained in step (d) is fed to a selective hydrogenation zone (20) so as to reduce its butadiene content to less than 10 parts per million with respect to the 1-butene present in said cut, (f) the effluent from step (e) is fed to a deisobutanization zone (22) in order to remove the major part of the isobutane contained therein, (g) the so deisobutanized fraction is subjected to a fractionation (zone 25) from which is recovered, on the one hand, a cut containing mainly 2-butenes and n-butane and, on the other hand, a fraction containing at least 99% by weight of 1-butene, (h) the mixture ($\alpha$) formed of gasoline and jet fuel base obtained in step (b) is admixed with the gasoline cut ($\gamma$) obtained in step (d) and with the $C_4$ cut, of high 2-butenes and n-butane content, obtained in step (g), the new resulting mixture being subjected to hydrogenation in zone (15), (i) the hydrogenation effluent of step (h) is subjected to at least one fractionation from which is recovered n-butane, a gasoline cut and a fuel cut.

3. A process according to claim 2 wherein, in the polymerization-disproportionation stage of step (a), at least 95% by weight of the isobutene are converted to a gasoline consisting essentially of isobutene dimers and trimers, a portion of said gasoline being converted, on the one hand to 2-butenes and 1-butene and, on the other hand, to a jet fuel base type cut with an isobutene trimers and tetramers base and wherein, in the so-called finishing polymerization zone of step (c), at least 90% by weight of the isobutene react whereas the total conversion of 2-butenes and 1-butene remains lower than or equal to 10% by weight.

4. A process according to claim 3, wherein said cut ($\beta$) further contains, by weight, less than 2% of isobutene and less than 500 ppm of butadiene.

5. A process according to claim 3, wherein said cut ($\delta$) further contains at least 0.15% by weight of isobutene.

6. A process according to claim 1, wherein the n-butane cut recovered during the fractionation of step (i) is fed to a steam-cracking zone.

7. A process according to claim 1, wherein the olefinic $C_4$ cut, treated according to the invention, is issued from a steam-cracking zone and wherein the n-butane cut recovered during the fractionation of step (i) is recycled to said steam-cracking zone.

8. A process according to claim 1 for producing 1-butene of high purity from a $C_4$ olefinic cut, characterized in that:

(a) a $C_4$ olefinic cut containing isobutane, n-butane, 1-butene, 2-butenes, isobutene and less than 2% by weight of butadiene, is subjected in a zone (4) to a polymerization-disproportionation, effected in liquid phase, during which, on the one hand, the isobutene of said cut is essentially converted, at least partly, to gasoline and, on the other hand, at least a portion of said gasoline is converted to 1-butene and 2-butenes, and to a jet fuel base type cut, (b) the effluent withdrawn from the polymerization-disproportionation zone (4) is subjected to a fractionation in zone (6) giving, on the one hand, a mixture ($\alpha$) of gasoline and jet fuel base and, on the other hand, a fraction ($\beta$) consisting essentially of isobutane, n-butane, 1-butene, 2-butenes, less than 5% by weight of isobutene and less than 2000 ppm of butadiene, (c) the fraction (β) obtained in step (b) is fed to a selective, called finishing polymerization zone (8) wherein at least 90% by weight of the isobutene contained therein is converted to gasoline, the selective polymerization reaction being effected in liquid phase, (d) the effluent from the finishing polymerization zone is subjected to a fractionation (zone 10) giving, on the one hand, a fraction (γ) consisting in major part of gasoline, containing dimers and trimers of isobutene and of 1- and 2-butenes and, on the other hand, a fraction (δ) consisting essentially of isobutane, n-butane, 1-butene, 2-butenes, less than 0.3% by weight of isobutene and less than 100 ppm of butadiene, (e) the fraction (δ) issued from step (d) is fed to a selective hydrogenation zone (20), so as to reduce its butadiene content to less than 10 parts per million with respect to the 1-butene present in said fraction, (f) the effluent from step (e) is fed to a deisobutanization zone (22) in order to remove the major part of the isobutane contained therein, (g) the so-deisobutanized fraction is subjected, in zone (25), to a fractionation giving, on the one hand, a cut containing in major part 2-butenes and n-butane and, on the other hand, a fraction consisting of at least 99% by weight of 1-butene, and (h) the mixture (α) consisting of gasoline and jet fuel base obtained in step (b) is admixed with the gasoline fraction (γ) obtained in step (d), the resulting new mixture being subjected, in zone (15), to a fractionation giving, on the one hand, a gasoline cut of high octane number and, on the other hand, a jet fuel cut.

9. A process according to claim 8, wherein, during the polymerization-disproportionation stage of step (a), at least 95% by weight of the isobutene reacts and is converted to a gasoline essentially formed of isobutene dimers and trimers, a portion of said gasoline being converted, on the one hand, to 2-butenes and 1-butene and, on the other hand, to a jet fuel base type cut, comprising essentially isobutene trimers and tetramers and, wherein, in the so-called finishing polymerization zone of step (c), at least 90% of the isobutene react whereas the total conversion of 2-butenes and 1-butene remains smaller than or equal to 10% by weight.

10. A process according to claim 8, wherein the fraction (β) further contains, by weight, less than 2% of isobutene and less than 500 ppm of butadiene.

11. A process according to claim 8, wherein the fraction (δ) further contains less than 0.15% by weight of isobutene.

12. A process according to claim 8, wherein, in addition, said jet fuel cut obtained at the end of the fractionation of step (h) is fed to a hydrogenation zone before being used as fuel.

13. A process according to claim 8, wherein the selective hydrogenation of step (e) is effected in the presence of a supported catalyst containing 0.05–0.5% by weight of palladium and from 0.05 to 1% by weight of silver, the ratio by weight silver/palladium being from 0.7:1 to 3:1.

14. A process according to claim 13, wherein the catalyst carrier is an alumina of a specific surface from 1 to 100 m²/g.

15. A process according to claim 8, wherein the polymerization-disproportionation of step (a) and the finishing polymerization of step (c) are effected in the presence of a silica-alumina catalyst.

16. A process according to claim 15, wherein the polymerization-disproportionation catalyst further contains 0.1 to 5% by weight of chromium oxide and the finishing polymerization catalyst further contains 0.1 to 5% by weight of zinc oxide.

17. A process according to claim 1, for the joint production of highly pure 1-butene, premium gasoline and jet fuel from a $C_4$ olefinic cut, wherein:

(a) a fresh charge consisting essentially of $C_4$ olefinic cut containing isobutane, n-butane, 1-butene, 2-butenes, isobutene and less than 2% by weight of butadiene, is subjected, in a zone (4), to a polymerization-disproportionation in liquid phase, during which a portion of the isobutene of said cut is essentially converted, at least partly, by isomerization, to gasoline, to a jet fuel base type cut and to 1-butene and 2-butenes, (b) the effluent withdrawn from the polymerization-disproportionation zone (4) is subjected in zone (6) to a fractionation giving, on the one hand, a mixture (α) of gasoline and jet fuel base and, on the other hand, a fraction (β) essentially consisting of isobutane, n-butane, 1-butene, 2-butenes, less than 5% by weight of isobutene and less than 2000 ppm by weight of butadiene, (c) the fraction (β) obtained in step (b) is fed to a selective polymerization zone (8) called finishing-polymerization zone, wherein at least 90% by weight of the isobutene contained therein are converted to gasoline, the selective polymerization reaction being effected in liquid phase, the total conversion of the 2-butenes and 1-butene being lower than or equal to 10% by weight, (d) the effluent from the finishing polymerization zone is subjected to a fractionation (zone 10) giving, on the one hand, a fraction (γ) consisting in major part of gasoline, containing in particular dimers and trimers of isobutene and of 1- and 2-butenes, and on the other hand, a fraction (δ) consisting essentially of isobutane, n-butane, 1-butene, 2-butenes, less than 0.3% by weight of isobutene and less 100 ppm by weight of butadiene, (e) the fraction (δ) issued from step (b) is fed to a selective hydrogenation zone (20) so as to reduce its butadiene content to less than 10 parts per million by weight with respect to the 1-butene present in said fraction, (f) the effluent from step (e) is fed to a deisobutanization zone (22) in order to remove at least the major part of the isobutane contained therein, (g) the so-deisobutanized fraction is subjected to a fractionation, in zone (25), giving, on the one hand, a cut (ε) containing in major part 2-butenes and n-butane and, on the other hand, a fraction consisting of at least 99% by weight of 1-butene, the process being characterized in that, thereafter, (h) said cut (ε) containing in major part 2-butenes and n-butane, issued from step (g), is fed through a line (27) to an isomerization zone (28) wherein at least a portion of said 2-butenes is isomerized to isobutene and to 1-butene, while maintaining unchanged the major part of the n-butane, (i) the product issued from the isomerization zone of step (h) is first fed to a fractionation zone (30) from the bottom of which is recovered a fraction containing mainly 1-butene, 2-butenes, isobutene, isobutane, n-butane and gasoline, said fraction being fed to a fractionation zone (33) from the bottom of which is recovered gasoline and at the top of which is withdrawn a mixture containing particularly isobutene, 1-butene, 2-butenes and isobutane, (j) said mixture, obtained in the preceding step at the top of the fractionation zone (33), is fed to a solvent extraction distillation zone (36) so as to recover a mixture containing mainly isobutene, 1-butene and 2-butenes which is recycled to the input of the polymerization-disproportionation zone (4), and (k) the mixture (α) of gasoline and jet fuel base issued from step (b) is combined, on the one hand, with the gasoline obtained at the bottom of the fractionation zone (33) of step (i) and, on the other hand, with the fraction (γ) obtained in step (d), the resultant mixture being fed to a fractionation zone (15) at the top of which is recovered a premium gasoline and from the bottom of which is recovered a jet fuel.

18. A process according to claim 17, wherein the jet fuel obtained in step (k) is then subjected to a hydrogenation.

19. A process according to claim 17, wherein, during step (h), said portion of 2-butenes is isomerized in the presence of steam, the molar ratio steam/hydrocarbons being from 0.2 to 2.

20. A process according to claim 19, wherein, in addition, the 2-butenes are isomerized in the presence of a catalyst containing fluorinated alumina.

21. A process according to claim 19, wherein, during the isomerization, at least 40% of the 2-butenes are converted to isobutene and 1-butene, whereas at least 80% of the n-butane remain unchanged.

22. A process according to claim 21, wherein at least 45% of the 2-butenes are converted whereas at least 90% of the n-butane remain unchanged.

* * * * *